US00PP27743P3

(12) United States Plant Patent
Grosser

(10) Patent No.: US PP27,743 P3
(45) Date of Patent: Mar. 7, 2017

(54) ***CITRUS* ROOTSTOCK NAMED 'UFR-16'**

(50) Latin Name: ***Citrus grandis*×*Citrus reticulata***
Varietal Denomination: UFR-16

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,425

(22) Filed: Jan. 5, 2015

(65) Prior Publication Data

US 2015/0195975 P1 Jul. 9, 2015

Related U.S. Application Data

(60) Provisional application No. 61/923,573, filed on Jan. 3, 2014.

(51) Int. Cl.
*A01H 5/08* (2006.01)

(52) U.S. Cl.
USPC ..... Plt./201

(58) Field of Classification Search
USPC ..... Plt./201
CPC ..... A01H 5/0806
See application file for complete search history.

(56) References Cited

PUBLICATIONS

Florida Foundation Seed Producers, Inc.; 9 New Citrus Rootstocks—Descriptions and Data; May 2014, 14 pages.*
U.S. Appl. No. 14/544,424, filed Jan. 5, 2015, Grosser.
U.S. Appl. No. 14/544,427, filed Jan. 5, 2015, Grosser.
U.S. Appl. No. 14/544,423, filed Jan. 5, 2015, Grosser.
U.S. Appl. No. 14/544,572, filed Jan. 22, 2015, Grosser.
U.S. Appl. No. 14/544,571, filed Jan. 22, 2015, Grosser.
U.S. Appl. No. 14/544,573, filed Jan. 22, 2015, Grosser.
U.S. Appl. No. 14/545,063, filed Mar. 20, 2015, Grosser.
U.S. Appl. No. 14/544,570, filed Jan. 22, 2015, Grosser.
Grosser et al., "Continued Development of Rootstocks Tolerant of the Phytophthora-Diaprepes Complex via Greenhouse Screening," *Proc. Fla. State Hort. Soc.* 120:103-109, 2007.
Grosser et al., "Protoplast fusion and citrus improvement," *Plant Breeding Reviews* 8:339-374, 1990.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Protoplast fusion for production of tetraploids and triploids: Applications for scion and rootstock breeding in citrus," *Plant Cell Tissue Organ Culture* 104:343-357, 2011.
Letter and corresponding informational document to Florida citrus nurseries for the purpose of a possible license agreement, dated Jan. 9, 2014.

* cited by examiner

*Primary Examiner* — Kent L Bell
(74) *Attorney, Agent, or Firm* — Dentons US LLP

(57) ABSTRACT

'UFR-16' is a new and distinct diploid citrus rootstock for improved disease resistance. 'UFR-16' has shown a positive reaction to the Huanglongbing disease (HLB, or citrus greening disease) in experimental field trials. Scion trees grafted on this rootstock initially show a reduced frequency of infection, and reduced disease symptoms once infected as compared to commercial diploid rootstocks. 'UFR-16' rootstock also showed tolerance to the *Diaprepes/Phytophthora* complex in greenhouse tests.

6 Drawing Sheets

BACKGROUND OF THE INVENTION

Latin name of the genus and species of the plant claimed: diploid hybrid of *Citrus grandis*×*Citrus reticulata.*

Variety denomination: 'UFR-16'.

The present invention relates to a new and distinct variety of citrus rootstock named 'UFR-16'. 'URF-16' is a diploid hybrid derived from a conventional cross of 'Hirado Buntan' pink pummelo×'Shekwasha' mandarin.

'UFR-16' was selected on the basis of its positive reaction to Huanglongbing disease (HLB, or citrus greening disease) in experimental field trials. The claimed plant was first asexually reproduced by grafting onto 'Swingle' citrumelo rootstock and planted in Wymama, Fla. The resulting trees were true to type. Scion trees grafted onto this rootstock initially show a reduced frequency of infection, and reduced disease symptoms once infected when compared to commercial diploid rootstocks. Scion trees grafted to 'UFR-16' rootstock grow off quickly and are vigorous in the field, producing medium to large trees comparable in size to trees on sour orange rootstock.

BRIEF SUMMARY OF THE INVENTION

'UFR-16' is seedy and partially polyembryonic, making it amenable to standard nursery propagation practices for uniform liner production, although seedling populations need to be carefully rogued to remove zygotics. 'UFR-16' has shown tolerance to the *Diaprepes-Phytophthora* complex in greenhouse tests. Based on its parentage, 'UFR-16' is expected to grow well on calcareous soils, and should also be tolerant of citrus blight. Long-term performance of scion trees on 'UFR-16' is unknown. Yield and fruit quality data is limited, and trees do not begin cropping until the 4th year. Tolerance to *Citrus tristeza* virus (CTV) is unknown, but scion trees infected with CTV that were grafted onto 'UFR-16' have shown normal growth in the greenhouse and field.

BRIEF DESCRIPTION OF THE DRAWINGS

'UFR-16' is illustrated by the accompanying photographs, which show the tree's from, foliage, and fruit. The colors shown are as true as can be reasonably obtained by conventional photographic procedures. The photographs are of a tree approximately 10-years old. All figures were taken during the fall of 2013 from the same tree.

DETAILED BOTANICAL DESCRIPTION

Figure 1:
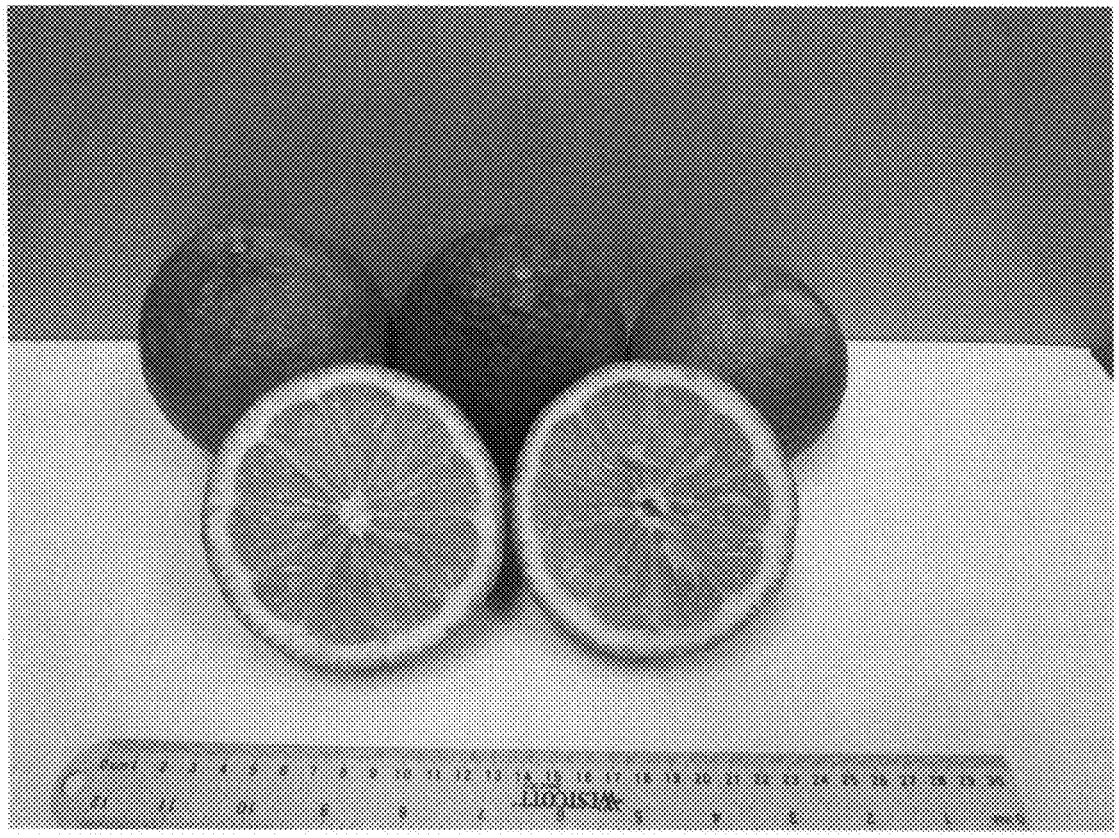
FIG. 1.—Shows a close-up of the nearly mature fruits with the rind and cross-sectional view of the fruit when cut in the center.
Figure 2:
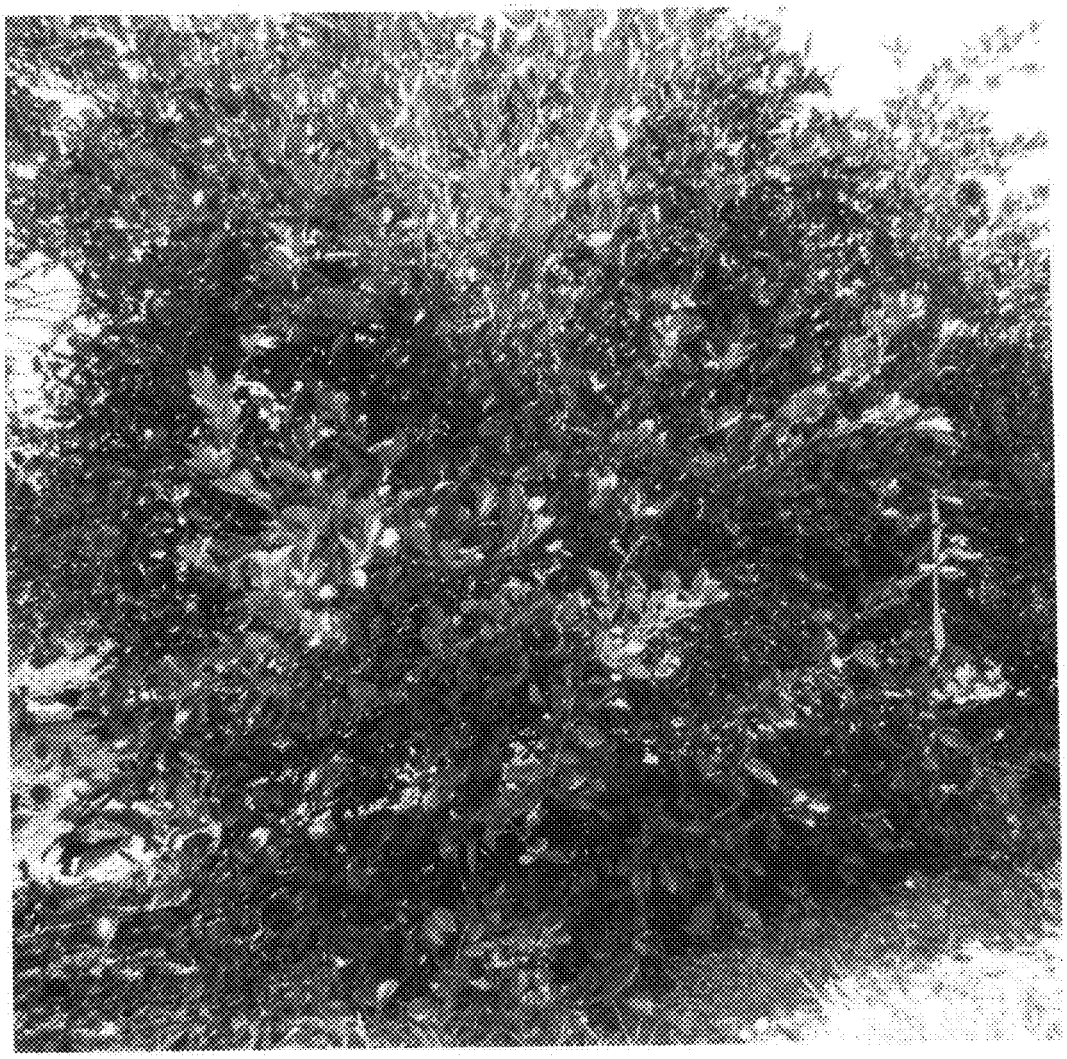
FIG. 2.—Shows the overall mature plant growth habit in the fall of 2013.
Figure 3:
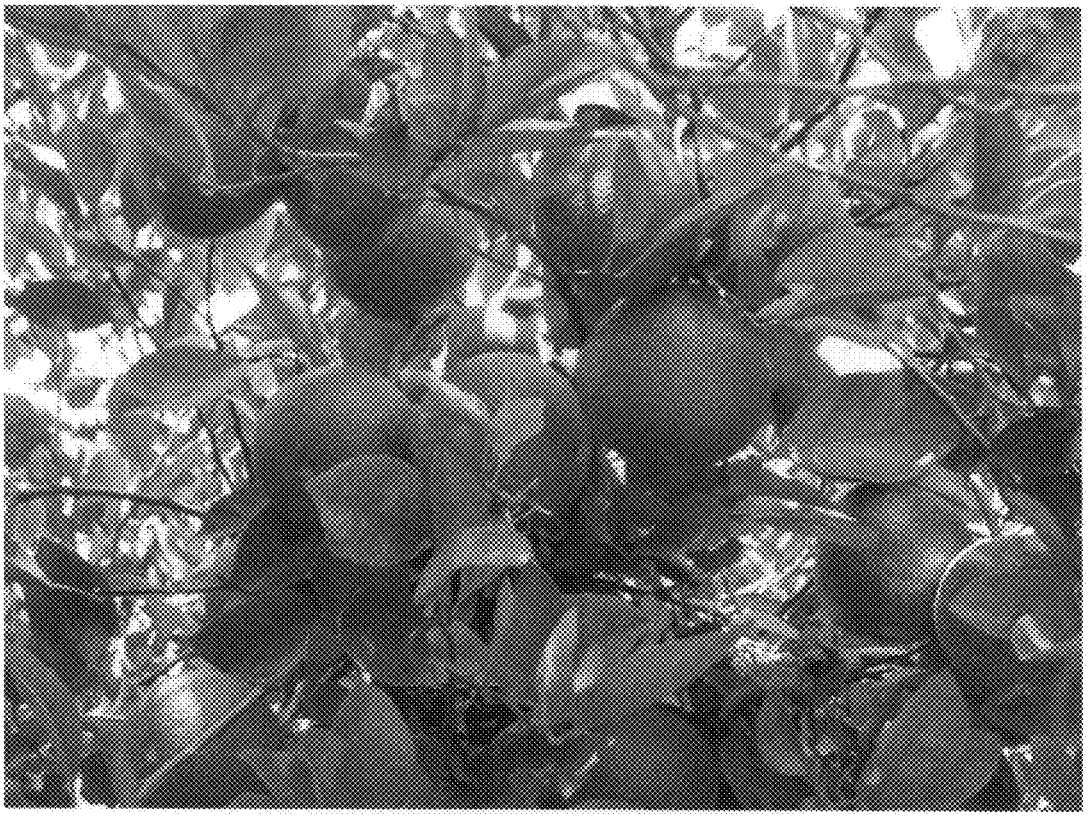
FIG. 3.—Shows nearly mature fruits hanging on the tree.
Figure 4:
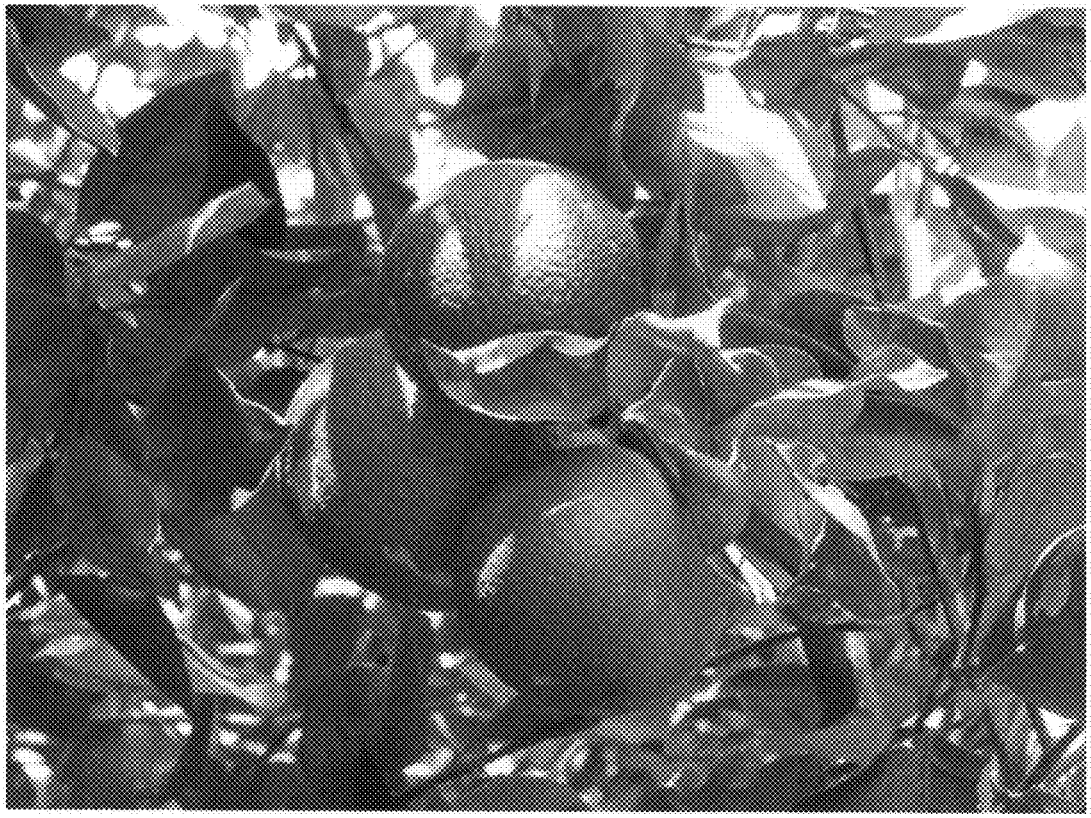
FIG. 4.—Shows a close-up of leaves and nearly mature fruits.
Figure 5:
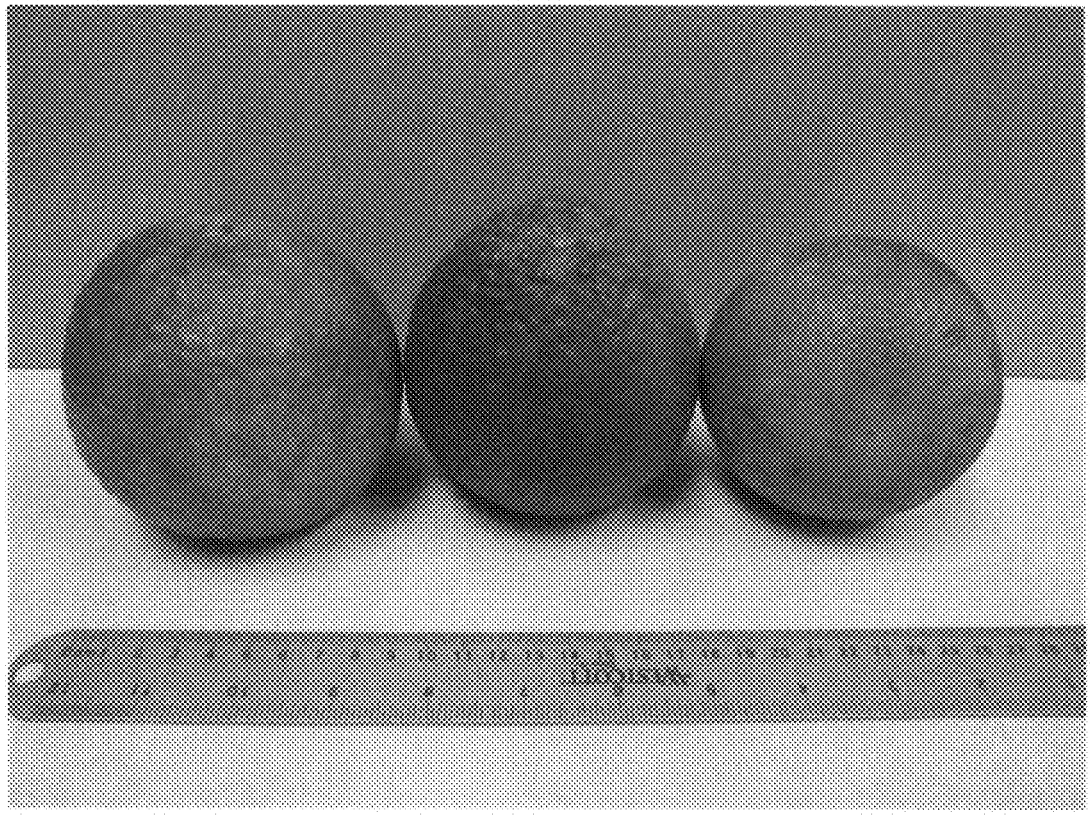
FIG. 5.—Shows a close-up of nearly mature fruits.
Figure 6:
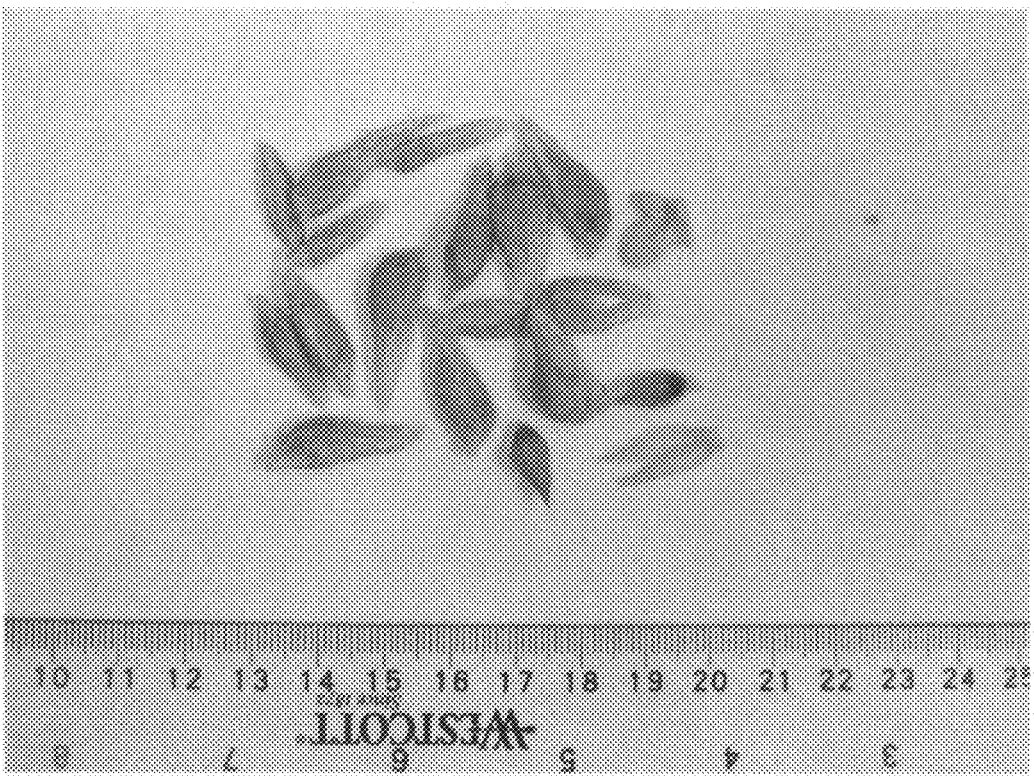
FIG. 6.—Shows a close-up of seeds from nearly mature fruit.

The following detailed description sets forth the distinctive characteristics of 'UFR-16'. The colors (except those in common terms) are described from The R.H.S. Colour Chart published by The Royal Horticultural Society in London (second edition), in association with the Flower Council of Holland.

Phenotypic Description of *Citrus reticulata* 'UFR-16'

Classification:

*Botanical.*—*Citrus depressa* (or *Citrus reticulata*)×*Citrus grandis.*

*Common name.*—Diploid pummelo×mandarin hybrid.

Parentage:

*Female parent.*—'Hirado Buntan' pink pummelo (unpatented).

*Male parent.*—'Shekwasha' mandarin (unpatented).

Tree:

*Ploidy.*—Diploid.

*Size.*—Medium large.

*Height.*—3.8 meters.

*Tree spread.*—3.5 to 3.8 meters.

*Vigor.*—Vigorous.

*Density.*—Canopies are quite dense.

*Form.*—The tree has a rounded shaped with both lateral and upright branches growing toward low to medium angles. Branches with fruit exhibit drooping.

*Growth habit.*—Both upright and lateral growth with low-medium angle.

Trunk:

*Trunk diameter.*—14.6 cm in diameter at 30 cm above ground on a 10-year-old tree.

*Trunk texture.*—Rough.

*Trunk bark color.*—RHS 197C (greyed-green); irregularly striated with RHS N137A (green).

Branches:

*Crotch angle.*—First crotch forms a 50- to 60-degree angle, middle crotch forms a 46-degree angle.

*Branch length.*—Branch reaches 3.8 meters from the first crotch to the tip of the branch.

*Branch texture.*—Relatively rough with small thorns or spines.

*Branch color* (*shoots from previous flush, hardened, and* 4 *to* 5 *mm in diameter*).—RHS N137A (green).

Leaves:

*Size* (*lamina average*).—Length: 126.5 mm. Width: 78 mm. L/W ratio: 1.62.

*Thickness.*—Thicker than regular and average compared to commercial mandarin hybrids, but thinner than regular pummelo hybrids.

*Type.*—Simple.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS N137A (green). Lower surface (abaxial): RHS 138A (green).

*Petiole.*—Shape: Brevipetiolate (shorter than leaf lamina); junction between petiole and lamina is articulate. Width (petiole wing): Narrow. Shape (petiole wing): Obovate. Length: 22.3 to 27.2 mm. Width: 3.8 to 5.7 mm. Color: RHS N137A (green).

Flowers and flower buds:

*Type.*—Hermaphrodite.

*Bearing.*—Flowers grow from leaf axillaries and leaf terminals singly and in small clusters; most single flowers grow from leaf axillaries.

*Flower bud size.*—Shape: Initial visible flower bud has a round ball shape; mature flower bud has an elongated olive shape.

*Flower petals.*—Shape: Flat, spatula-shaped. Apex shape: Smooth, acute-shaped. Base shape: Even obtuse. Margin: Smooth.

*Flower sepal.*—Shape: Delta-shaped with an acute angle at the apex. Apex shape: Triangle-shaped. Margin: Smooth.

*Fragrance.*—Fragrant/Moderately fragrant.

*Reproductive organs.*—Fertility: Appears self-fertile. Pollen amount: Abundant/Moderate amount. Pollen color (general): Bright-yellow. Ovary shape: Oval-shaped.

Fruit:

*Size.*—Uniform.

*Height.*—94 to 103 mm on average.

*Width.*—96 to 103.6 mm on average.

*Average weight* (*per individual fruit*).—442 grams.

*Shape.*—Round; some fruits are slightly bell shaped.

*Shape* (*cross-section*).—Round.

*Apex.*—Truncated with slight dent.

*Apex cavity diameter.*—N/A.

*Base cavity diameter.*—8.5 to 10 mm.

*Base.*—Most fruits have no neck, although some have a short neck and are bell-shaped.

*Harvesting.*—Fruit can be harvested in October in Florida, and will hold on the tree through December.

*Fruit stem* (*short stem connecting the fruit*).—Length: 8.3 mm. Diameter: 5.7 mm. Color: RHS 146C (yellow-green) with RHS 195B (greyed-green) strip.

Skin:

*Adherence.*—Adherence between albedo (mesocarp) and flesh (endocarp) is medium. The adherence is evenly distributed from base to apex.

*Thickness.*—6.5 to 8.3 mm on average.

*Texture.*—Smooth.

*Color*.—Flavedo (epicarp): Ranges between RHS 154B (yellow-green) to RHS 151B (yellow-green). Albedo (mesocarp): RHS 155B (white).

*Stylar end*.—Closed.

*Rind oil cell density*.—42 oil cells/square cm.

Flesh:

*Number of segments*.—Between 10 and 11 segments per fruit on average.

*Segment walls*.—Medium-firm with sufficient strength to maintain integrity as separated.

*Juice*.—Abundant.

*Color*.—Uniformly RHS 158A (yellow-white).

*Texture*.—Medium soft.

*Vesicles*.—Length: Arranged from 18.4 to 21.9 mm on average. Diameter (thickness): 4.7 to 5.4 mm on average.

*Eating quality*.—N/A.

*Juice index*.—Soluble solids (average): 8.0 Brix.

Seeds:

*Type*.—Partially polyembryonic.

*Number*.—Ranges from 15 to 20. Occasionally some fruit contains less than 15 seeds.

*Shape*.—Seed shapes are not uniform. Normal seeds are mostly ventricose/swollen shaped and clavate club shaped.

*Size*.—Length: 22 to 25.2 mm. Width: 7.1 to 8.5 mm.

*Seed coat color*.—Outer Surface: RHS 155B (white) and wrinkled. Inner surface: RHS 165C (greyed-orange). Cotyledon color: RHS 145D (yellow-green).

Resistance to disease: 'UFR-16' rootstock was selected on the basis of its positive reaction to HLB disease (huanglongbing or citrus greening disease) in field trials. Trees on this rootstock initially show a reduced frequency of infection, and reduced disease symptoms once infected when compared to commercial diploid rootstocks. 'UFR-16' rootstock also showed tolerance to the *Diaprepes/Phytophthora* complex in greenhouse tests.

What is claimed is:

1. A new and distinct citrus rootstock plant as illustrated and described herein.

* * * * *